United States Patent [19]

Kanda

[11] 4,071,406
[45] Jan. 31, 1978

[54] PROCESS FOR PRODUCING XANTHOMONAS POLYSACCHARIDE ON A SOYBEAN WHEY MEDIUM

[75] Inventor: Hiroshi Kanda, Zushi, Japan

[73] Assignee: The Nisshin Oil Mills, Ltd., Tokyo, Japan

[21] Appl. No.: 705,491

[22] Filed: July 15, 1976

[30] Foreign Application Priority Data

July 15, 1975 Japan .................................. 50-85857

[51] Int. Cl.$^2$ ...................... C12D 13/04; C12B 3/04; C12B 3/14
[52] U.S. Cl. ................................. 195/31 P; 195/100
[58] Field of Search ................. 195/96, 31 P, 100, 99, 195/114

[56] References Cited

U.S. PATENT DOCUMENTS

| 3,485,719 | 12/1969 | Rogovin | 195/31 P |
| 3,594,280 | 7/1971 | Colin et al. | 195/31 P |
| 3,671,398 | 6/1972 | Colin et al. | 195/31 P |

OTHER PUBLICATIONS

Chiyonobu et al., "A New Growth Effecting Peptide of Bacillus Species from Soybean Cake", Agr. Biol. Chem. vol. 38, No. 4, (1974), pp. 847–854.

Levine et al., A Compilation of Culture Media, The Williams & Wilkins Co., Baltimore, (1930), pp. 192, 689, 690, 770.

Primary Examiner—Alvin E. Tanenholtz
Assistant Examiner—Thomas G. Wiseman
Attorney, Agent, or Firm—Sughrue, Rothwell, Mion, Zinn and Macpeak

[57] ABSTRACT

A soybean whey liquid is obtained by extracting water soluble constituents from defatted soybeans with water, precipitating proteins at the isoelectric point with acids and neutralizing the resulting supernatent liquid with an alkali.

This soybean whey liquid contains a very small amount of vitamins and unknown growth factors as well as sucrose, stachyose, water-soluble proteins and minerals. When a culture medium of the soybean whey liquid having sugars added therein is used for the culture of the bacterium *Xanthomonas campestris*, *Xanthomonas polysaccharide* is obtained with good yield.

6 Claims, No Drawings

PROCESS FOR PRODUCING XANTHOMONAS POLYSACCHARIDE ON A SOYBEAN WHEY MEDIUM

BACKGROUND OF THE INVENTION

This invention relates to a process for the production of *Xanthomonas polysaccharide* and particularly, to an improved fermentation medium for producing this polysaccharide by growing the bacterium *Xanthomonas campestris.*

The *Xanthomonas polysaccharide* has been developed mainly in the United States of America and used for industrial purposes such as an emulsion stabilizer, lubricants, latex and others.

A process for the production of Xanthomonas polysaccharide (hereinafter referred to as Xanthan gum) includes, in general, culturing the bacterium *Xanthomonas campestris* in a medium consisting of glucose or sucrose as a carbon source, distillers dried solubles or defatted soybeans as a protein source and minerals such as potassium phosphate and magnesium sulphate. Such a process is disclosed, for example, in U.S. Pat. No. 3,485,719.

On the other hand, a waste liquor which is obtained in the isolation of soybean proteins is known as a soybean whey. The soybean whey can be obtained, for example, by a process of extracting water soluble constituents from defatted soybeans with water, precipitating proteins at the isoelectric point (a pH of about 4.5) with acids and neutralizing the resulting supernatant liquid, by a process of washing defatted soybeans with an aqueous alcohol to remove beany flavor and distilling alcohol off therefrom, or as a waste liquor which is obtained by cooking soybeans in the boiling water. The soybean whey contains nutritious water soluble constituents, such as sucrose, raffinose, stachyose, water-soluble proteins, organic acids, vitamins, minerals and others.

Therefore the soybean whey has, hitherto, been employed in a concentrated form as a feed, or used as a culture medium for yeasts. Besides, it has been provided for recovering water-soluble proteins of good quality. Such utilizations, however, are unprofitable because the worths of the products obtained are low economically.

SUMMARY OF THE INVENTION

An object of this invention is to provide a culture medium containing the soybean whey as a protein source for the production of the Xanthan gum by fermentation thereby utilizing the soybean whey effectively.

Another object of this invention is to provide a process for producing the Xanthan gum with good yield in a short time, using a culture medium containing the soybean whey.

In accordance with this invention, the Xanthan gum is obtained by culturing the bacterium *Xanthomonas campestris* in a medium comprising sugars digestible for the bacterium, such as glucose and sucrose and a soybean whey liquid obtained by extracting water soluble constituents from defatted soybeans with water.

DETAILED DESCRIPTION OF THE INVENTION

It has been found that a very good medium for the culture of the strain of *Xanthomonas campestris* can be obtained by adding an appropriate amount of sugars to the soybean whey liquid which is prepared from the extraction of defatted soybeans with water.

The soybean whey liquid which may be used in this invention is, preferably, obtained by adding 10 - 30 fold, preferably 15 - 20 fold water to defatted soybeans to extract the water-soluble constituents, adjusting a pH to about 4.5 with acids such as phosphoric acid, hydrochloric acid, sulfuric acid or organic acids, removing the proteins precipitated by means of centrifuge or the like, and neutralizing the resulting supernatant liquid to a pH of about 7.0 with addition of an alkali such as ammonia, sodium hydroxide and potassium hydroxide.

A composition of the soybean whey liquid obtained may vary dependent on the extraction temperature and the solvent ratio for extraction (the amount of water added).

By way of example, the composition of a soybean whey obtained by extracting with 20 fold water at 40° C is given as follows:

| | |
|---|---|
| Total solid content: | 1.5% (W/V) |
| Total sugar content: | 0.5% |
| Sucrose | 0.20% |
| Raffinose: | 0.07% |
| Stachyose: | 0.20% |
| Other sugars: | 0.03% |
| Proteins: | 0.25% |
| Ashes: | 0.55% |
| Other constituents:* | 0.2% |

*Contained lecithin, gums, vitamins, unknown growth factors and others.

The culture medium is provided by adding sugars digestible for the bacteria, such as glucose and sucrose to the soybean whey liquid. An amount of the sugars added is such that an available sugar content in the culture medium is within the range of 0.5 to 5.0%, preferably 1.0 to 3.0 W/V %. The sugar digestible for the bacteria, which is present in the soybean whey is only sucrose. The sucrose content varies dependent on the extraction solvent ratio, e.g., it is about 0.3% for a 15 fold water extraction and about 0.2% for a 20 fold water extraction. Therefore an available sugar content of the medium may be indicated by the total content of the sucrose present in the soybean whey and the added glucose or sucrose. The available sugar content is indicated by W/V % in a value calculated as glucose.

According to this invention, it has also been found that the optimum ratio of sugar content to nitrogen content in the culture medium, which is considered to be important for the growth of the bacterium, is within the range of 100 : 1 to 100 : 3 (the sugar content being calculated as glucose).

The culture medium is sterilized in the conventional method and then the strain of the species *Xanthomonas campestris* is cultivated under the aerobic condition at temperatures of 25° to 30° C for 24 - 72 hours. A viscosity of the culture solution obtained thus is within the range of 1,000 - 11,000 cps. If the viscosity is below 1000 cps, the culture solution is too dilute and therefore not economical. With the viscosity over 11,000 cps, the stirring of the culture solution is difficult.

A yield of Xanthan gum against sugar is given as follows:

$$\frac{\text{Xanthan gum content (W/V \%)}}{\text{Available sugar content (W/V \%)}} \times 100\ (\%)$$

According to this invention, for example, when the culture is effected using the soybean whey obtained from a 20 fold water extraction as a protein source of the medium as set forth in Example 1, a yield of 85 – 90% is obtained for a 1% available sugar content during 24 hours, a yield of 80 – 85% for a 2% available sugar content during 40 hours, and a yield of 60 – 65% for a 3% available sugar content during 70 hours. A fermentation time can be further reduced with use of a jar fermenter as set forth in Example 2.

On the contrary, when the same culture as the above is effected using the conventional media which contain glucose, distillers dried solubles or defatted soybean, potassium phosphate and magnesium sulphate, a yield of 80 – 85% is obtained for a 1% available sugar content during 80 hours, a yield of 65 – 70% for a 2% available sugar content during 60 hours, and a yield of 50 – 55% for a 3% available sugar content during 96 hours.

As is apparent from the foregoing, the medium of this invention is superior in yield and fermentation time to the conventional mediums.

The reason why the end product can be obtained with good yield in a short time by using the medium of this invention is not made clear, but it should be understood that this invention is not bound by the following theoretical explanation:

Since the distillers dried solubles and the defatted soybeans contain a large amount of proteins (about 40 – 50%), a small amount of the protein source used is quite enough to maintain the balance to the sugar content in the abovementioned optimum ratio (i.e. 100 : 1 to 100 : 3). Accordingly, the medium includes naturally a very small amount of unknown growth factors and vitamins which are present in the protein source used. On the contrary, when the soybean whey liquid obtained by extracting the defatted soybean with 10 – 30 fold water and removing a large portion of the proteins precipitated is used as the protein source, the amount of the unknown growth factors and vitamins involved in the soybean whey liquid increases several times as compared with the use of the defatted soybean itself as the protein source.

In the preferred embodiment of this invention, the extraction solvent ratio (the amount of water added) for obtaining the soybean whey is within the range of 15 to 20 fold and the available sugar content in the medium is within the range of 1 to 3%.

Also, it is apparent from the optimum ratio of sugar content to nitrogen content in the medium that when the extraction solvent ratio is large, the nitrogen content of the soybean whey becomes smaller and therefore the corresponding sugar content must be reduced. On the other hand, when the extraction solvent ratio is small, the nitrogen content of the soybean whey becomes larger and therefore the corresponding sugar content must be increased.

It should be understood that this invention provides an epoch-making process for obtaining the Xanthan gum with good yield in a short time as compared with the conventional media, using the soybean whey which has hitherto not been known as the medium for the preparation of the Xanthan gum.

This invention, also, provides a very effective utilization for the soybean whey for which available uses have not been found so far.

This invention will be illustrated by the following non-limitative examples.

EXAMPLE 1

Each of 10 fold, 15 fold, 20 fold and 30 fold water was added to a defatted soybean to extract water soluble constituents sufficiently at 40° C and adjusted to pH 4.5 with a 1.5% phosphoric acid solution. By means of centrifuge, a supernatant liquid was obtained and the precipitated proteins and other insoluble matters were removed. Soybean whey liquids corresponding to each of the extraction solvent ratios were obtained by neutralizing the supernatant liquid to a pH of 7.0 with addition of a 10% solution of potassium hydroxide.

To each of the soybean whey liquids there was added glucose in such amounts that an available sugar content inclusive the content of sucrose present in the whey is 0.5%, 1.0%, 2.0%, 3.0% and 4.0% (W/V), respectively. Each of 50 cc whey was poured to a 300 cc flask, sterilized at 121° C for 10 minutes and cooled.

To the medium obtained, there was added 5% of a culture solution of the strain B 1459 of the bacterium *Xanthomonas campestris* which had previously been subjected to a shaken culture in YM medium *[1] at 28° C for 24 hours. Then a shaken culture was effected at 28° C till glucose had been consumed.

*[1] YM medium: malt extract 0.3%, yeast extract 0.3%, glucose 1%, peptone 0.5%

Viscosity of the whey media obtained thus, concentration of the Xanthan gum, yield against sugar and fermentation time are given in Table 1.

Analysis of the Xanthan gum was effected in accordance with S. P. Rogovin, J. Biochem. Microbiol. Tech. and Eng. Vol. 3, 51 – 63 (1961) by deducting a value obtained in the same analysis from a non-fermented soybean whey as a control.

The viscosity was measured by Brookfield viscometer at 30 r.p.m.

Table 1

| Extraction Solvent Ratio | Available Sugar Content W/V % | Viscosity cps | Xanthan Gum Concentration W/V % | Yield against Sugar % | Fermentation Time hr. |
|---|---|---|---|---|---|
| | 0.5 | 300 | 0.25 | 50 | 24 |
| 10 fold | 1.0 | 1000 | 0.55 | 55 | 24 |
| water | 2.0 | 5200 | 1.32 | 66 | 48 |
| | 3.0 | 7000 | 1.52 | 51 | 70 |
| | 4.0 | 9400 | 1.74 | 44 | 96 |
| | 0.5 | 750 | 0.45 | 90 | 24 |
| 15 fold | 1.0 | 1700 | 0.78 | 78 | 24 |
| water | 2.0 | 7800 | 1.55 | 78 | 48 |
| | 3.0 | 10800 | 1.88 | 63 | 70 |
| | 4.0 | 11000 | 1.90 | 48 | 96 |
| | 0.5 | 800 | 0.46 | 92 | 24 |
| 20 fold | 1.0 | 2200 | 0.85 | 85 | 24 |
| water | 2.0 | 8600 | 1.66 | 83 | 40 |
| | 3.0 | 10500 | 1.86 | 62 | 70 |
| | 4.0 | 10800 | 1.88 | 47 | 96 |

Table 1-continued

| Extraction Solvent Ratio | Available Sugar Content W/V % | Viscosity cps | Xanthan Gum Concentration W/V % | Yield against Sugar % | Fermentation Time hr. |
|---|---|---|---|---|---|
| 30 fold water | 0.5 | 750 | 0.45 | 90 | 24 |
| | 1.0 | 2050 | 0.82 | 82 | 24 |
| | 2.0 | 6500 | 1.47 | 74 | 40 |
| | 3.0 | 7000 | 1.52 | 51 | 70 |
| | 4.0 | 7600 | 1.59 | 40 | 96 |

Table 1 shows that the yield against sugar is reduced when the extraction solvent ratio is smaller than 15 fold and that when the available sugar content is increased to about 4% or more, the stirring of the culture becomes difficult because of the high viscosity and therefore the yield against sugar is reduced.

For comparison, with the conventional medium the culture of the strain B 1459 of *Xanthomonas campestris* was effected in the same procedure. The results are given in Table 2.

Composition of the medium used is as follows:

| | |
|---|---|
| Glucose: | 0.5, 1.0, 2.0, 3.0, 4.0 (W/V %) |
| Distillers dried solubles: | 0.5 |
| Potassium phosphate: | 0.5% |
| Magnesium sulphate: | 0.01% |

Table 2

| Sugar Content W/V % | Viscosity cps | Xanthan Gum Concentration W/V % | Yield against Sugar % | Fermentation Time hrs. |
|---|---|---|---|---|
| 0.5 | 850 | 0.48 | 96 | 24 |
| 1.0 | 2100 | 0.84 | 84 | 30 |
| 2.0 | 5800 | 1.40 | 70 | 60 |
| 3.0 | 7500 | 1.58 | 53 | 96 |
| 4.0 | 8000 | 1.62 | 41 | 120 |

EXAMPLE 2

1 kg of a defatted soybean meal was added with 20 kg of water and stirred with a mixer at 40° C to dissolve water-soluble constituents sufficiently. Thereafter a pH was adjusted to 4.5 with addition of a 10% solution of hydrochloric acid to precipitate proteins. 17.5 kg of a soybean whey liquid were obtained by removing centrifugally the precipitated proteins.

This whey liquid was neutralized to a pH of 7.0 with sodium hydroxide, then added with 320 g of glucose and poured to a jar fermenter. Sterilizing was effected at 120° C for 10 minutes.

To the medium obtained, there were added 800 cc of a culture solution of the strain B 1459 of *Xanthomonas campestris* which had previously been precultured for 24 hours, and an aerating culture was effected at 28° C till glucose had been consumed.

A concentration of the Xanthan gum in the medium was 1.65%. Yield against sugar: 82.5%, Fermentation time: 32 hours.

What we claim is:

1. A process for the production of Xanthomonas Polysaccharide which comprises culturing a strain of the bacterium *Xanthomonas campestris* in a soybean whey medium and recovering the *Xanthomonas polysaccharide*, said soybean whey medium being obtained by extracting water soluble constituents from defatted soybeans with water to give an aqueous product, precipitating proteins from the resulting aqueous product at the isoelectric point with acids, removing the proteins thus precipitated to obtain a supernatant liquid, neutralizing the resulting supernatant liquid with an alkali, and then adding to the resulting soybean whey liquid an amount of glucose and/or sucrose suitable for the culture of *Xanthomonas campestris*.

2. The process of claim 1, wherein said defatted soybeans are extracted with 10 – 30 fold water in the preparation of the soybean whey medium.

3. The process of claim 1, wherein the amount of glucose and/or sucrose added is such that the available sugar content of the soybean whey medium is within the range of 0.5 to 5.0 W/V %, calculated as glucose.

4. The process of claim 1, wherein said defatted soybeans are extracted with 15 to 20 fold water and the amount of glucose and/or sucrose added is such that the available sugar content of the soybean whey medium is within the range of 1.0 to 3.0 W/V %, calculated as glucose.

5. The process of claim 1, wherein cultivation is under aerobic conditions at 25° to 30° C for 24 to 72 hours.

6. The process of claim 1, wherein the soybean medium has a viscosity within the range 1,000 to 11,000 cps.

* * * * *